US008747808B2

(12) United States Patent
Reutelingsperger et al.

(10) Patent No.: US 8,747,808 B2
(45) Date of Patent: Jun. 10, 2014

(54) RADIOLABELED ANNEXINS

(75) Inventors: Christiaan Peter Maria Reutelingsperger, Maastricht (NL); Peter Jozef Jacobus Moonen, Susteren (NL)

(73) Assignee: MosaMedix B.V., Kattendijke (NL)

( * ) Notice: Subject to any disclaimer, the term of this patent is extended or adjusted under 35 U.S.C. 154(b) by 478 days.

(21) Appl. No.: 13/060,667

(22) PCT Filed: Aug. 26, 2009

(86) PCT No.: PCT/NL2009/050513
§ 371 (c)(1),
(2), (4) Date: May 19, 2011

(87) PCT Pub. No.: WO2010/024673
PCT Pub. Date: Mar. 4, 2010

(65) Prior Publication Data
US 2011/0251486 A1    Oct. 13, 2011

(30) Foreign Application Priority Data

Aug. 26, 2008  (EP) ..................................... 08162959

(51) Int. Cl.
| A61K 51/00 | (2006.01) |
| A61M 36/14 | (2006.01) |
| A61K 51/08 | (2006.01) |
| A61K 38/02 | (2006.01) |
| A61K 38/03 | (2006.01) |
| A61K 38/04 | (2006.01) |
| A61K 49/00 | (2006.01) |
| C07K 7/08 | (2006.01) |

(52) U.S. Cl.
CPC ............ *A61K 51/087* (2013.01); *A61K 38/02* (2013.01); *A61K 38/03* (2013.01); *A61K 38/04* (2013.01); *A61K 49/0002* (2013.01); *A61K 51/08* (2013.01); *C07K 7/08* (2013.01)
USPC ......... 424/1.69; 424/1.11; 424/1.65; 424/9.1; 530/300; 530/324; 530/325; 530/350

(58) Field of Classification Search
CPC . A61K 51/04; A61K 51/0497; A61K 51/087; A61K 51/088; A61K 51/08; A61K 51/00; A61K 38/00; A61K 38/02; A61K 38/03; A61K 38/04; A61K 38/16; A61K 2121/00; A61K 49/00; A61K 49/0002; A61K 49/0004; C07K 14/00; C07K 7/00; C07K 7/02; C07K 7/04; C07K 7/06; C07K 7/08
USPC .......... 424/1.11, 1.49, 1.65, 1.69, 1.73, 1.81, 424/1.85, 1.89, 9.1, 9.3, 9.4, 9.5, 9.6; 530/300, 350, 324, 325; 514/1, 1.1
See application file for complete search history.

(56) References Cited

U.S. PATENT DOCUMENTS 6,323,313 B1 * 11/2001  Tait et al. ...................... 530/324
7,635,676 B2 * 12/2009  Allison .......................... 514/1.1

FOREIGN PATENT DOCUMENTS

| JP | 2006-316004 A | 11/2006 |
| WO | WO-98/48699 A1 | 11/1998 |
| WO | WO-2005/086955 A2 | 9/2005 |
| WO | WO2006/003488 | * 1/2006 |
| WO | WO-2006/003488 A2 | 1/2006 |
| WO | WO-2007-069895 A1 | 6/2007 |

OTHER PUBLICATIONS

Andree et al., Binding of Vascular Anticoagulant α (VACα) to Planar Phospholipid Bilayers, Journal of Biological Chemistry, 1990, pp. 4923-4928.
Jung et al., "I-124 Labled Recombinant Human Annexin V Produced by *E. coli* for Apoptosis Image Using Small Animal PET," Journal of Nuclear Medicine, vol. 49 (Supplement 1), 2008, p. 304.
Tabata et al., "Expression and Purification of Recombinant Human Annexin A2 in *Pichia pastoris* and Utility of Expression Product for Detecting Annexin A2 Antibody," Journal of Bioscience and Bioengineering, vol. 101, No. 2, 2006, pp. 190-197.
Van Genderen et al., "In Vitro Measurement of Cell Death with the Annexin A5 Affinity Assay," Nature Protocols, vol. 1, No. 1, 2006, pp. 363-367.
Tait, J. F. et al., "Development and Characterization of Annexin V Mutants with Endogenous Chelation Sites for $^{99m}$Tc", Bioconjugate Chem., 2000, vol. 11, No. 6, pp. 918-925, XP009003666.
Waibel, R. et al., "Stable one-step technetium-99m labeling of His-tagged recombinant proteins with a novel Tc(I)-carbonyl complex", Nature Biotechnology, Sep. 1999, vol. 17, pp. 897-901, XP-002548771.
Tait, J. F. et al., "Structural Requirements for In Vivo Detection of Cell Death with $^{99m}$Tc-Annexin V", The Journal of Nuclear Medicine, May 2005, vol. 46, No. 5, pp. 807-815, XP-002510935.
Berndorff, D. et al., "Imaging of Tumor Angiogenesis Using $^{99m}$Tc-Labeled Human Recombinant Anti-ED-B Fibronectin Antibody Fragments", The Journal of Nuclear Medicine, Oct. 2006, vol. 47, No. 10, pp. 1707-1716, XP-002510936.
Cortez-Retamozo, V. et al., "$^{99m}$Tc-Labeled Nanobodies: A New Type of Targeted Probes for Imaging Antigen Expression", Current Radiopharmaceuticals, 2008, vol. 1. No. 1, pp. 37-41, XP-002510937.
Biechlin, M-L. et al., "Improvement in radiolabelling proteins with the $^{99m}$Tc-tricarbonyl-core [$^{99m}$Tc(CO)$_3$]$^+$, by thiol-derivatization with iminothiolane: application to γ-globulins and annexin V", Journal of Label Compd Radiopharm, 2005, vol. 48, pp. 873-885, XP-002510938.
Search Report mailed Oct. 16, 2009 in International Application No. PCT/NL2009/050513.

* cited by examiner

*Primary Examiner* — D L Jones
(74) *Attorney, Agent, or Firm* — Gilberto M. Villacorta; Sunit Talapatra; Foley & Lardner LLP

(57) ABSTRACT

A radiolabeled annexin comprising at least 2 up to 20 histidine residues at its N-terminus is disclosed. At least two of said histidine residues are adjacent or separated by no more than one other amino acid. The radiolabeled annexin is a stable complex with a radionuclide such as technetium 99m. The radiolabeled annexin can be used in a method of imaging cell death in a nucleated cell within a region of a mammalian subject in vivo.

18 Claims, 2 Drawing Sheets

FIG. 1. (SEQ ID No. 7)

```
            10          20          30          40
AQVLRGTVTD FPGFDERADA ETLRKAMKGL GTDEESILTL 50          60          70          80
LTSRSNAQRQ EISAAFKTLF GRDLLDDLKS ELTGKFEKLI 90         100         110         120
VALMKPSRLY DAYELKHALK GAGTNEKVLT EIIASRTPEE 130         140         150         160
LRAIKQVYEE EYGSSLEDDV VGDTSGYYQR MLVVLLQANR 170         180         190         200
DPDAGIDEAQ VEQDAQALFQ AGELKWGTDE EKFITIFGTR 210         220         230         240
SVSHLRKVFD KYMTISGFQI EETIDRETSG NLEQLLLAVV 250         260         270         280
KSIRSIPAYL AETLYYAMKG AGTDDHTLIR VMVSRSEIDL 290         300         310         319
FNIRKEFRKN FATSLYSMIK GDTSGDYKKA LLLLCGEDD
```

FIG. 2 (SEQ ID No. 8)

```
                 16         26         36         46
HHHHHH AQVLRGTVTD FPGFDERADA ETLRKAMKGL GTDEESILTL 56         66         76         86
LTSRSNAQRQ EISAAFKTLF GRDLLDDLKS ELTGKFEKLI 96        166        116        126
VALMKPSRLY DAYELKHALK GAGTNEKVLT EIIASRTPEE 136        146        156        166
LRAIKQVYEE EYGSSLEDDV VGDTSGYYQR MLVVLLQANR 176        186        196        206
DPDAGIDEAQ VEQDAQALFQ AGELKWGTDE EKFITIFGTR 216        226        236        246
SVSHLRKVFD KYMTISGFQI EETIDRETSG NLEQLLLAVV 256        266        276        286
KSIRSIPAYL AETLYYAMKG AGTDDHTLIR VMVSRSEIDL 296        366        316        325
FNIRKEFRKN FATSLYSMIK GDTSGDYKKA LLLLCGEDD
```

RADIOLABELED ANNEXINS

FIELD OF THE INVENTION

The invention relates to annexin molecules having binding sites for heavy metals, in particular radioactive metals. The invention further relates to the use of radiolabeled annexin molecules in diagnostic imaging.

BACKGROUND

Molecular Imaging of the biomarker phosphatidylserine (PS) in vivo is important for diagnosis of diseases and assessment of efficacy of therapy. Effective PS-recognising agents are annexin A5 and its variants. Technetium-labeled annexin A5 can be injected into a subject and, subsequently, Single Photon Emission Tomography (SPECT) can be applied to assess the biomarker PS. In order to assess the biomarker PS sensitively and specifically, it is mandatory that the complex between technetium and annexin A5 is stable in vivo and is rapidly cleared from the blood circulation.

Current complexes of technetium and annexin A5 are based on chemical bonding of Tc (technetium) to a non-specific site of the annexin molecule. For example, JP2006-316004 discloses a compound obtained by bonding 4'-aminomethyl-N,N'-trimethylene-dibenzohydroxamide to annexin V through a linker, which compound is capable of complexing technetium. WO 98/48699 discloses a complex in which Tc99m is linked to the annexin via succinimidyl hydrazinonicotinate (HYNIC). Such complexes suffer from insufficient stability. Moreover, it is not possible to direct the label at a specific site of the annexins, especially a site which does not interfere with its affinity profile. Jung et al., *J. Nucl. Med.* 2008 49 (Supplement 1):304P, refers to a 1-124 labeled recombinant annexin molecule for apoptosis imaging using small animal PET (positron emission tomography).

SUMMARY OF THE INVENTION

The present invention provides a novel annexin variant with an extension of its N-terminus carrying histidine residues to allow stable complex formation between a radionuclide such as technetium and annexin. The invention also pertain to such annexins carrying a radionuclide, i.e. to radiolabeled annexins. The invention furthermore provides annexin radiolabeled complexes for use in diagnostics and therapy.

BRIEF DESCRIPTION OF THE DRAWINGS

FIG. 1 (SEQ ID No. 7) depicts an annexin variant in accordance with the invention. The underlined amino acids correspond to the concave side of the annexin molecule.

FIG. 2 (SEQ ID No. 8) depicts another annexin variant in accordance with the invention.

DESCRIPTION OF THE INVENTION

Thus, the invention pertains to a (radiolabeled) annexin, which comprises a minimum of 2 and a maximum of 20 histidine residues at its N-terminus. In particular, the annexin of the invention comprises a minimum of 3, preferably at least 4 histidine residues at its N-terminus. The maximum number is not very critical, and practically it may be up to 12, or preferably up to 10 or even up to 8 histidine residues at the N-terminus.

Preferably, the histidine residues are contiguous, i.e. without other amino acids in between, or with only one amino acid in between. This particularly applies to two or three histidine residues. Thus, preferred partial sequences at the N-terminus include H-H; H-H-H; H-X-H; H-X-H-H; H-H-X-H; H-X-H-H; or H-X-H-H. An intervening amino acid X, if present at all, is preferably not a large apolar amino acid such as Phe, Tyr, Leu, Ile or Val, or Met or Cys. Preferably, intervening amino acids, if present at all, are selected from Gly, Ala, Ser, Lys, and Arg, and in cases of two or more X, these may be different. Most preferably, the annexin variant of the invention comprises at least 3 contiguous histidine residues at its N-terminus, especially at the very terminus.

The term "annexin" refers to any protein capable of binding to phospholipids, especially phosphatidylserine (PS) in a calcium-dependent manner, and members of the so-called annexin family. These substances have the property of binding to negatively charged phospholipids, preferably with a dissociation constant less than $10^{-6}$ M in the presence of $Ca^{2+}$ ions. The family covers many members; information thereon and on the protein and nucleotide sequences can for example be found on http://www.structuralchemistry.org/annexins/seq/search.php. A sequence alignment of various annexins is also to be found in WO 2007/069895, which is incorporated herein by reference. A preferred example is annexin A5, having the amino acid sequence of SEQ ID No. 7 (FIG. 1), but other annexins can also be used for producing and using the annexin variants of the invention. For example, annexins A4 and A8 can also be used. Where reference is made to the amino acid sequence and the positions of annexin A5, this also applies to the other annexins, especially human annexins, by choosing the corresponding position. The corresponding positions are known to the skilled person and can be easily identified, e.g. using the triplet DAE (Asp-Ala-Glu) at positions 19-21 of A5, which is conserved over most annexins, with minor deviations in some annexins, e.g. to DAQ in A4, A9 and A10. The annexins may originate from any species, preferably avian or mammalian, more preferably mammalian, most preferably human.

Wild-type annexins only have a limited number of histidine residues, and never two or more with no or only one other amino acid in between (H-H or H-X-H). For example, wild-type mammalian annexins A5 only contain His residues at positions 97, 204 and 266. Hence, the presence of between 2 and 20 histidine residues with a maximum of one intervening other amino acids is a unique feature of the annexin variants of the present invention.

As used herein, the N-terminus of the annexin variants comprises the sequence upstream of the glutamic acid (E) residue at position 16 of SEQ ID No. 7, or corresponding regions in other annexins. In particular, the annexin variants of the invention have the N-terminal sequences No 1-6, in increasing order of preference:

| | |
|---|---|
| X1-ERADAETLRKAMK | (SEQ ID No. 1) |
| X2-GFDERADAETLRKAMK | (SEQ ID No. 2) |
| X3-DFPGFDERADAETLRKAMK | (SEQ ID No. 3) |
| X4-TVTDFPGFDERADAETLRKAMK | (SEQ ID No. 4) |
| X5-LRGTVTDFPGFDERADAETLRKAMK | (SEQ ID No. 5) |
| X6-AQVLRGTVTDFPGFDERADAETLRKAMK | (SEQ ID No. 6) | wherein:

each of $X_1$-$X_6$ comprises between 2 and 20 histidine residues separated by no more than one other amino acid residue, and $X_1$ represents a sequence of at least 15 amino acids;
$X_2$ represents a sequence of at least 12 amino acids;
$X_3$ represents a sequence of at least 9 amino acids;
$X_4$ represents a sequence of at least 6 amino acids;
$X_5$ represents a sequence of at least 3 amino acids;
$X_6$ represents a sequence of at least 2 amino acids.

Herein, the part starting with the first E (Glu) of SEQ ID No. 1 (=position 16 in SEQ ID No. 7) can be different in other annexins. For example, it is AMEDAQTLRKAMK in human A4, and PDPDAETLYKAMK in human A8. Exchanges of single amino acids in that part corresponding to other annexins are allowed, for example an exchange of Glu (E) at position 16 by Ala (A) or Pro (P).

In a special embodiment of the invention, the annexin variant carries one or more, preferably one up to three cysteine residues, most preferably just one cysteine residue, at the concave side of the annexin molecule. The concave side of the annexin molecule corresponds to the underlined amino acids in the sequence of FIG. 1 (SEQ ID. No. 7). Thus, the cysteine residue is preferably present at one of the positions 1-19, 24, 28, 46-64, 86-89, 118-135, 150, 157-170, 202-219, 245-248, and 280-294 of annexin A5 or corresponding positions of other annexins.

It is at the same time preferred, that the annexin variant does not carry cysteine residues at the convex side of the molecule. This means that e.g. in annexin A5, the (only) cysteine residue at position 315 is preferably substituted by another amino acid, such as Ser, Ala or Val. Details about the positions of the cysteine molecule and the manner of introducing them can be found in WO 2006/003488, which is incorporated herein by reference.

A specifically preferred polyhistidine annexin variant of the invention is the annexin variant having the amino acid sequence depicted in FIG. 2 (SEQ ID No.8), or a variant which contains 3, 4, 5, 7, 8, 9 or 10 N-terminal His residues instead of the 6 as depicted. Further preferred variants are those having the amino acid sequence of FIG. 2, wherein one of the amino acids at positions 7-25, 30, 34, 52-70, 92-95, 124-141, 156, 163-176, 208-225, 251-254, and 286-300. Other preferred variant are those, which contains a Cys residue at one of the amino acids at the positions mentioned here above (7-25 etc.) of FIG. 2, wherein further the cysteine residue at position 321 is substituted by another amino acid, especially Ser, Thr, Ala or Val.

Further amino acid substitutions may be present in the annexin variants and radiolabeled annexins of the invention. For example, an amino acid substitution at one or more of the positions 16-29, 59-74, 88-102, 135-145, 156-169, 202-231, 259-266 and 305-317 of annexin A5 (or the positions which are each six higher in the poly-His annexin A5 variant of FIG. 2) may be substituted so as to inhibit internalisation of the annexin variant into the target cell, if so desired. Such substitution is preferably a substitution of a polar amino acid by an apolar one, as described in WO 2007/069895. Other amino acid substitutions are also allowed, provided that they do not significantly hamper the binding of the annexin to phosphatidylserine. This provision is deemed to be met if the substitution is a substitution by an amino acid present at the same position in another annexin type, especially if the other type is annexin A4 of A8, or in an annexin of the same type from another species.

The desired amino acid additions or substitutions can be performed by recombinant techniques well-known in the art and illustrated in the examples below. The histidine residues can be introduced into the DNA encoding the annexin variant of the invention by substitution of two or more codons encoding N-terminal amino acids by histidine encoding codons (CAU/CAT or CAC), for example substitution of codons for N-terminal AQV (Ala-Gln-Val) of annexin A5 by three histidine codons.

Alternatively, or additionally, the annexin-encoding gene can be extended at its N-terminus with two or more, e.g. 3, 4, 5 or 6, histidine codons. Extension of annexin molecules as such is known in the art. For example, WO2005/086955 discloses a human annexin V homodimer with a 6-His tag, and Tabata et al., *J. Biosc. Bioeng.* 1001 (2006) 190-197, describes a 6-His-tagged annexin A2. Polyhistidine derivatives can be produced by recombinant methods known in the art. They are conventionally used for purification purposes and often contain additional amino acids facilitating removal of the polyhistidine tag by specific proteolysis. In contrast, the polyhistidine variants are not to be proteolysed, and preferably do not contain such additional specific proteolysis sites. Vectors for producing polyhistidine tags are commercially available, e.g. from Qiagen, Venlo, NL.

If desired, a codon for any one of the underlined amino acids in FIG. 1, for example the codon encoding Phe at position 11, can be substituted by a cysteine codon and/or the Cys codon at position 315 can be substituted by a codon for another amino acid, for example Ser. The modified annexin gene can then be expressed in a suitable host to produce the desired annexin variant of the invention.

The cysteine residue can be used to couple pharmacological agents or further diagnostic agents to the annexin. A linker such as N-succinimidyl 3-(2-pyridyldithio)propionate, N-succinimidyl maleimidoacetate, N-succinimidyl 3-maleimidopropionate, pyridyl, maleimide-containing groups, halogen-containing groups, can be used to couple the agent to the Cys residue. The pharmacological agent can e.g. be selected from a toxin, an enzyme, a lipid, a carbohydrate, an immunoglobulin or a fragment thereof, an immunoconjugate, a chemotherapeutic compound, a photosensitizer, a radionuclide, a cell death inducing agent, a cell death inhibiting agent, a fibrinolytic compound. The (further) diagnostic compound can be selected from e.g. a fluorescent group, a contrast agent, a photosensitiser, an ultrasound agent etc. Further details are described in WO 2006/003488.

The presence of at least two histidine residues allows the annexin variant of the invention to bind a radionuclide, especially a metal radionuclide. Herein, the histidine residues act as multifunctional chelators for the (metal) radionuclide. Thus, the invention also pertains to a radiolabeled annexin, which is a complex of a histidine-substituted annexin variant as described above and a radionuclide. The radionuclide is preferably biocompatible and is preferably selected from Gallium 67, Gallium 68, Indium 111, Technetium 99m, Rhenium 188, Copper 64 and Tin 117m. Most preferably, the radionuclide in the radiolabeled annexin according to the invention is $Tc^{99m}$ or $Re^{188}$, most especially $Tc^{99m}$.

The radionuclides can be coupled to the histidine-containing annexin variants in a manner known in the art. For example, the variant can be contacted with a tricarbonyl complex of the radionuclide such as technetium or rhenium to produce a radionuclide-linked annexin. For $^{99m}Tc$ tricarbonyl, a reagent kit is commercially available (Mallinckrodt, Petten, NL).

The radiolabeled annexin can be used in a method of imaging cell death in a nucleated cell within a region of a mammalian subject in vivo. Such a method can comprise:

(a) administering said radiolabeled annexin to the subject,
(b) positioning the subject within the detection field of a radiation detector device, and
(c) measuring radiation emission from the radionuclide in the subject, with the radiation detector device, to construct an image of radiation emission, wherein said image is a representation of cell death in said nucleated cell of said mammalian subject.

In step (a) of this method, a radiolabeled annexin (e.g. technetium 99m-labeled annexin V) is administered to the subject using standard protocols. A period of time is then allowed to achieve localisation of the radiolabeled annexin in the subject. Then, in optional step (b), the subject is placed within the detection field of a radiation detector device. The subject is maintained in a substantially immobilised condition while radiation from the radionuclide is measured using the radiation detector device (step c). The measured data are then processed to an image of the radiation emission. The image thus obtained can be used to provide the attending clinician with a map or a localisation of areas of cell death in the mammalian subject, or in the region of the mammalian subject that is being analysed.

The radiolabeled annexin may be administered in several ways. In a preferred embodiment, the radiolabeled annexin is administered intravenously. Alternatively, it can be administered intraperitoneally. A further option is to administer the labeled annexin intrathecally. Also, the radiolabeled annexin can be administered intrapleurally. Further methods of administration comprise intralymphatic administration, or, alternatively, intramuscular administration.

The dosage of radiolabeled annexin to be administered depends on the radionuclide used, on the tissue of organ which is targeted, and on the conditions of the diagnosis and the subject. Preferably, the radiolabeled annexin is administered in an amount which results in a dose of between about 3 and about 30 mCi. Technetium 99m can be administered to adult humans at doses up to about 20 mCi. The preferred dose for a single Tc99m administration is between about 5 and 20 mCi, preferably between 7.5 and 15 mCi. The amounts of other radionuclides can be determined accordingly.

The amount of radiolabeled annexin to be administered (calculated on the basis of the amount of annexin as such) is preferably at least 0.3 µg/kg body weight, and below 300 µg/kg. Typically, the amount is less than about 100 µg/kg. Preferably, the amount is between 0.5 and 20 µg/kg, most preferably between 1 and 20 µg/kg.

After the radiolabeled annexin is administered, it is allowed to be localised to the target tissue or organ. When an equilibrium or a quasi-equilibrium between localised and non-localised or unbound annexin is achieved, usually between 10 and 240 minutes, especially between 20 and 120 minutes, the measurement can start. If necessary, the state of localisation as a function of time may be followed by imaging the radiation signal from the labeled annexin. Where the radionuclide is technetium 99m, the radiation will be γ emission. WO 98/48699, which is incorporated herein by reference, gives further information and examples of imaging cell death in a mammalian subject.

Preferred uses for radiolabeled annexins include the detection of inappropriate apoptosis in diseased states, where it is undesired, e.g. immune disorders such as Lupus, transplant rejection, or in cells subject to ischemia; and the detection of insufficient apoptosis where it is desired, e.g., tumours or cells infected with a virus. In particular, the cell death is caused by necrosis.

The radiolabeled annexin can be used in a variety of clinical settings in which apoptotic and/or necrotic cell death is to be monitored, such as organ and bone marrow transplant rejection or injury, infectious and non-infectious inflammatory diseases, autoimmune disease, cerebral and myocardial infarction and ischemia, cardiomyopathies, athero-sclerotic conditions, neural and neuromuscular degenerative diseases, sickle cell disease, β-thalassemia, cancer therapy, AIDS, myelodysplastic syndromes, and toxin-induced liver disease, etc. Radiolabeled annexins are also useful as a clinical research tool to study the normal immune system, embryological development, and immune tolerance and allergy.

Radiolabeled annexin V can be used, for example, to image and quantify apoptotic cell death in normal and malignant tissues undergoing treatment. Monitoring apoptosis with serial imaging studies using radiolabeled annexin can be used for the rapid testing and development of new drugs and therapies in a variety of diseases. In addition, the methods may be used to monitor the progress of treatment, monitor the progress of disease, or both. Further, they may be used to aid in early detection of certain diseases.

The region of the mammalian subject where cell death is to be imaged in vivo, may be any part, tissue or organ of the subject. In particular, said region is in an organ of said subject or a portion thereof. In a preferred embodiment of the invention, the region is in the head of said subject or a portion thereof. In another preferred embodiment, said region is in the heart of said subject or a portion thereof. In a further specific embodiment, said region is in the liver of said subject or a portion thereof. The region wherein (desired) cell death is to be imaged can especially be in a tumour in the mammalian subject or a portion thereof. Also, the region (of undesired) cell death can be a transplant in the subject or a portion thereof. Further, said region can be in an ischemic site in said subject or a portion thereof.

The imaging can be performed using methods and equipment known in the art. For example, the radiation detector device is a positron emission detector device, in case of use of e.g. $Cu^{64}$ as a radionuclide. For gamma-radiating radionuclides, such as $Tc^{99m}$, $Sn^{117m}$ and $Re^{188}$, gamma ray imaging devices can be used. The signals can be detected, enhanced, processed, using standard techniques. For example, single photon emission computed tomography (SPECT) may be used with the types gamma-emitting radionuclides described herein, e.g., $Tc^{99m}$.

Example 1

Annexin A5 with an N-Terminal Extension of 6 histidine Residues Binds to Phosphatidylserine The 5'-end of the cDNA of annexin A5 was extended with 6 nucleotide triplets each encoding histidine (CAT or CAC) using standard molecular cloning techniques known by a person skilled in the art. The cDNA of annexin A5 can either encode human wild-type annexin A5 or a variant thereof.

The extended cDNA is cloned into a prokaryotic expression vector suitable for production of the histidine-extended annexin A5 (His-anxA5) by bacteria. Other expression systems such as eukaryotic expression systems can also be used to produce the His-anxA5. The cDNA is then cloned into an expression vector suitable for eukaryotic expression systems.

The bacterially produced His-anxA5 is purified from the other bacterial constituents by employing the metal-binding property of the histidine residues. The mixture of proteins is adjusted to 5-20 mM of imidazole and this mixture is applied to nickel or cobalt affinity chromatography. After washing the bound His-anxA5 is eluted from the column by a gradient of 50-1000 mM imidazole. The eluted His-anxA5 has a high purity (>90% pure) and can be used for biological analysis.

The phosphatidylserine-binding properties of His-anxA5 are comparable to wild-type annexin A5 as analysed by ellipsometry (Andree et al. JBC 1990) and flow cytometry of apoptotic cells (Van Genderen et al. Nature Prot. 2006, 363). Hence, extension of the N-terminal tail of annexin A5 with 6 histidine residues does not alter the biological property to bind to phosphatidylserine.

Example 2

Radiolabeling of Histidine Extended Annexin A5

His-anxA5 was labeled with the radionuclide $^{99m}$Technetium using the commercially available Isolink kit and following the instructions of the manufacturer of Isolink (Mallinckrodt, Petten, the Netherlands). Analysis by size-exclusion chromatography (BioSep-SEC-S3000) showed that both the radiochemical purity and radiochemical yield of $^{99m}$Technetium-labeled His-anxA5 was more than 95%. The high yield and purity avoid a necessity of purification steps following radiolabeling.

Example 3

Stability of Radiolabeled Histidine Extended Annexin A5

His-anxA5 was radiolabeled with $^{99m}$Technetium as described by example 2. $^{99m}$Technetium labeled His-anxA5 was incubated in blood plasma during 1-24 hours at 37° C. Subsequent analysis revealed that $^{99m}$Technetium-labeled His-anxA5 is stable in blood plasma and neither decomposes nor causes transchelation of plasma proteins, e.g. transfers the $^{99m}$Technetium isotope to other plasma proteins. This stability is extremely important to its use as a nuclear agent in nuclear imaging technologies.

Example 4

Binding of $^{99m}$Technetium Labeled His-anxA5 to Apoptotic Cells In Vitro

His-anxA5 was radiolabeled with $^{99m}$Technetium as described by example 2. T-lymphoma cells (Jurkat cells) were cultured in vitro and triggered to execute apoptosis and expose phosphatidylserine. The treated Jurkat cells were mixed with $^{99m}$Technetium labeled His-anxA5, incubated for 5-30 minutes and centrifuged to a pellet. The supernatant was separated from the cells. Part of the cells were resuspended in calcium containing buffer (0.5-10 mM $CaCl_2$) and measured for radioactivity. Part of the cells was resuspended in EDTA containing buffer (1-10 mM EDTA) and recentrifuged. The resulting supernatant was measured for radioactivity. These analyses demonstrated that $^{99m}$Technetium labeled His-anxA5 has biological properties to bind in a calcium-dependent manner to apoptotic cells and phosphatidyserine that are comparable to annexin A5.

Example 5

Nuclear Imaging of Apoptosis using $^{99m}$Technetium Labeled His-anxA5 in a Mouse Model of Liver Apoptosis Mice were treated with intravenous injection of anti-Fas antibody or cycloheximide in order to induce liver apoptosis. 30-120 minutes following injection of the apoptosis inducer, $^{99m}$Technetium labeled His-anxA5 was injected intravenously. $^{99m}$Technetium labeled His-anxA5 was prepared as described by example 2. 30-240 minutes following injection of $^{99m}$Technetium labeled His-anxA5 SPECT analysis was performed. Thereafter the liver was taken out for analysis by autoradiography and immunohisto-chemical staining of caspase 3. The results demonstrate that it is possible to image non-invasively cell death using $^{99m}$Technetium labeled His-anxA5.

Example 6

Nuclear Imaging of Apoptosis using $^{99m}$Technetium Labeled His-anxA5 in a Mouse Model of Cancer Mice were injected in the flank with Daudi cells or Granta519 cells. After 4-6 weeks visible tumours had developed. The mice were injected intravenously with $^{99m}$Tc-labeled His-anxA5 was injected intravenously that was prepared as described by example 2. The uptake of $^{99m}$Tc labeled His-anxA5 by the tumour was measured non-invasively by SPECT. The mice were then treated with a cytostatic such as doxorubicin and cyclophosphamide. 24-72 hours following treatment the mice were injected intravenously $^{99m}$Tc labeled His-anxA5. Uptake by tumour was assessed non-invasively by SPECT. The results demonstrated that the efficacy of anti-tumour therapy can be assessed non-invasively using Tc labeled His-anxA5.

The invention claimed is:

1. A radiolabeled annexin, comprising a metal radionuclide bound to at least one of 2 to 20 histidine residues at the N-terminus of an annexin molecule, at least two of the histidine residues being adjacent or separated by no more than one other amino acid, and in which the annexin molecule carries one or more cysteine residues at the concave side of the annexin molecule.

2. The radiolabeled annexin according to claim 1, in which the radionuclide is selected from the group consisting of Gallium 67, Gallium 68, Indium 111, Technetium 99m, Rhenium 188, Copper 64 and Tin 117m.

3. The radiolabeled annexin according to claim 2, in which the radionuclide is $^{99m}$Technetium.

4. The radiolabeled annexin according to claim 1, which comprises from 3 up to 10 histidine residues at its N-terminus.

5. The radiolabeled annexin according to claim 1, in which said histidine residues are located upstream of the Glu residue at position 16 of SEQ ID No. 7.

6. The radiolabeled annexin according to claim 1, comprising the N-terminal sequence:
X4-TVTDFPGFDERADAETLRKAMK (SEQ ID No. 4) wherein X4 is said histidine residues and is a sequence of at least 6 amino acids.

7. The radiolabeled annexin according to claim 1, in which one of any of the amino acids at positions 1-19, 24, 28, 46-64, 86-89, 118-135, 150, 157-170, 202-219, 245-248, and 280-294 of SEQ ID No. 7 is replaced by a cysteine residue.

8. The radiolabeled annexin according to claim 7, in which said cysteine residue is coupled to a pharmacological agent.

9. A method of imaging cell death in a nucleated cell within a region of a mammalian subject in vivo, the method comprising:
(a) administering to the subject the radiolabeled annexin according to claim 1,
(b) measuring radiation emission from the radionuclide to construct an image of radiation emission,
wherein the image forms a representation of cell death in said nucleated cell of the subject.

10. The method according to claim 9, further comprising positioning the subject within the detection field of a radiation detector device.

11. The method according to claim 10, comprising administering the labelled annexin in an amount between about 1 and 10 µg annexin protein/kg.

12. The method according to claim 10, wherein the region is the head, heart, or liver of said subject or a portion thereof.

13. The method according to claim 10, wherein the region is in a tumour, transplant, and/or ischemic site in said subject or a portion thereof.

14. The radiolabeled annexin according to claim 1, which does not carry cysteine residues at the convex side of the annexin molecule.

15. The radiolabeled annexin according to claim 1, wherein said one or more cysteine residues at the concave side of the annexin molecule is bound to a pharmacological or diagnostic agent.

16. The radiolabeled annexin according to claim 1, wherein the histidine residues are separated by an amino acid other than histidine, methionine or cysteine.

17. The radiolabeled annexin according to claim 1, comprising the amino acid sequence of SEQ ID No. 8.

18. The radiolabeled annexin according to claim 17, wherein at least one amino acid at positions 7-25, 30, 34, 52-70, 92-95, 124-141, 156, 163-176, 208-225, 251-254 and 286-300 is substituted by a cysteine residue and the cysteine residue at position 321 is substituted by another amino acid.

* * * * *

SEQUENCE LISTING

```
<160> NUMBER OF SEQ ID NOS: 8

<210> SEQ ID NO 1
<211> LENGTH: 13
<212> TYPE: PRT
<213> ORGANISM: Artificial
<220> FEATURE:
<223> OTHER INFORMATION: N-terminus is a sequence of at least 15 amino
      acids and includes between 2 and 20 histidine residues separated
      by no more than one other amino acid residue

<400> SEQUENCE: 1

Glu Arg Ala Asp Ala Glu Thr Leu Arg Lys Ala Met Lys
1               5                   10
```

```
<210> SEQ ID NO 2
<211> LENGTH: 16
<212> TYPE: PRT
<213> ORGANISM: Artificial
<220> FEATURE:
<223> OTHER INFORMATION: N-terminus is a sequence of at least 12 amino
      acids and includes between 2 and 20 histidine residues separated
      by no more than one other amino acid residue

<400> SEQUENCE: 2

Gly Phe Asp Glu Arg Ala Asp Ala Glu Thr Leu Arg Lys Ala Met Lys
1               5                   10                  15

<210> SEQ ID NO 3
<211> LENGTH: 19
<212> TYPE: PRT
<213> ORGANISM: Artificial
<220> FEATURE:
<223> OTHER INFORMATION: N-terminus is a sequence of at least 9 amino
      acids and includes between 2 and 20 histidine residues separated
      by no more than one other amino acid residue

<400> SEQUENCE: 3

Asp Phe Pro Gly Phe Asp Glu Arg Ala Asp Ala Glu Thr Leu Arg Lys
1               5                   10                  15

Ala Met Lys

<210> SEQ ID NO 4
<211> LENGTH: 22
<212> TYPE: PRT
<213> ORGANISM: Artificial
<220> FEATURE:
<223> OTHER INFORMATION: N-terminus is a sequence of at least 6 amino
      acids and includes between 2 and 20 histidine residues separated
      by no more than one other amino acid residue

<400> SEQUENCE: 4

Thr Val Thr Asp Phe Pro Gly Phe Asp Glu Arg Ala Asp Ala Glu Thr
1               5                   10                  15

Leu Arg Lys Ala Met Lys
            20

<210> SEQ ID NO 5
<211> LENGTH: 25
<212> TYPE: PRT
<213> ORGANISM: Artificial
<220> FEATURE:
<223> OTHER INFORMATION: N-terminus is a sequence of at least 3 amino
      acids and includes between 2 and 20 histidine residues separated
      by no more than one other amino acid residue

<400> SEQUENCE: 5

Leu Arg Gly Thr Val Thr Asp Phe Pro Gly Phe Asp Glu Arg Ala Asp
1               5                   10                  15

Ala Glu Thr Leu Arg Lys Ala Met Lys
            20                  25

<210> SEQ ID NO 6
<211> LENGTH: 28
<212> TYPE: PRT
<213> ORGANISM: Artificial
<220> FEATURE:
<223> OTHER INFORMATION: N-terminus is a sequence of at least 2 amino
      acids and includes between 2 and 20 histidine residues separated
      by no more than one other amino acid residue

<400> SEQUENCE: 6
```

```
Ala Gln Val Leu Arg Gly Thr Val Thr Asp Phe Pro Gly Phe Asp Glu
1               5                   10                  15

Arg Ala Asp Ala Glu Thr Leu Arg Lys Ala Met Lys
                20                  25
```

<210> SEQ ID NO 7
<211> LENGTH: 319
<212> TYPE: PRT
<213> ORGANISM: Homo sapiens

<400> SEQUENCE: 7

```
Ala Gln Val Leu Arg Gly Thr Val Thr Asp Phe Pro Gly Phe Asp Glu
1               5                   10                  15

Arg Ala Asp Ala Glu Thr Leu Arg Lys Ala Met Lys Gly Leu Gly Thr
                20                  25                  30

Asp Glu Glu Ser Ile Leu Thr Leu Leu Thr Ser Arg Ser Asn Ala Gln
                35                  40                  45

Arg Gln Glu Ile Ser Ala Ala Phe Lys Thr Leu Phe Gly Arg Asp Leu
        50                  55                  60

Leu Asp Asp Leu Lys Ser Glu Leu Thr Gly Lys Phe Glu Lys Leu Ile
65                  70                  75                  80

Val Ala Leu Met Lys Pro Ser Arg Leu Tyr Asp Ala Tyr Glu Leu Lys
                85                  90                  95

His Ala Leu Lys Gly Ala Gly Thr Asn Glu Lys Val Leu Thr Glu Ile
                100                 105                 110

Ile Ala Ser Arg Thr Pro Glu Glu Leu Arg Ala Ile Lys Gln Val Tyr
            115                 120                 125

Glu Glu Glu Tyr Gly Ser Ser Leu Glu Asp Asp Val Val Gly Asp Thr
130                 135                 140

Ser Gly Tyr Tyr Gln Arg Met Leu Val Val Leu Leu Gln Ala Asn Arg
145                 150                 155                 160

Asp Pro Asp Ala Gly Ile Asp Glu Ala Gln Val Glu Gln Asp Ala Gln
                165                 170                 175

Ala Leu Phe Gln Ala Gly Glu Leu Lys Trp Gly Thr Asp Glu Glu Lys
            180                 185                 190

Phe Ile Thr Ile Phe Gly Thr Arg Ser Val Ser His Leu Arg Lys Val
            195                 200                 205

Phe Asp Lys Tyr Met Thr Ile Ser Gly Phe Gln Ile Glu Glu Thr Ile
210                 215                 220

Asp Arg Glu Thr Ser Gly Asn Leu Glu Gln Leu Leu Leu Ala Val Val
225                 230                 235                 240

Lys Ser Ile Arg Ser Ile Pro Ala Tyr Leu Ala Glu Thr Leu Tyr Tyr
                245                 250                 255

Ala Met Lys Gly Ala Gly Thr Asp Asp His Thr Leu Ile Arg Val Met
            260                 265                 270

Val Ser Arg Ser Glu Ile Asp Leu Phe Asn Ile Arg Lys Glu Phe Arg
            275                 280                 285

Lys Asn Phe Ala Thr Ser Leu Tyr Ser Met Ile Lys Gly Asp Thr Ser
            290                 295                 300

Gly Asp Tyr Lys Lys Ala Leu Leu Leu Leu Cys Gly Glu Asp Asp
305                 310                 315
```

<210> SEQ ID NO 8
<211> LENGTH: 325
<212> TYPE: PRT
<213> ORGANISM: Artificial
<220> FEATURE:

<223> OTHER INFORMATION: annexin variant

<400> SEQUENCE: 8

```
His His His His His Ala Gln Val Leu Arg Gly Thr Val Thr Asp
1               5                   10                  15

Phe Pro Gly Phe Asp Glu Arg Ala Asp Ala Glu Thr Leu Arg Lys Ala
                20                  25                  30

Met Lys Gly Leu Gly Thr Asp Glu Glu Ser Ile Leu Thr Leu Leu Thr
            35                  40                  45

Ser Arg Ser Asn Ala Gln Arg Gln Glu Ile Ser Ala Ala Phe Lys Thr
        50                  55                  60

Leu Phe Gly Arg Asp Leu Leu Asp Asp Leu Lys Ser Glu Leu Thr Gly
65                  70                  75                  80

Lys Phe Glu Lys Leu Ile Val Ala Leu Met Lys Pro Ser Arg Leu Tyr
                85                  90                  95

Asp Ala Tyr Glu Leu Lys His Ala Leu Lys Gly Ala Gly Thr Asn Glu
                100                 105                 110

Lys Val Leu Thr Glu Ile Ile Ala Ser Arg Thr Pro Glu Glu Leu Arg
            115                 120                 125

Ala Ile Lys Gln Val Tyr Glu Glu Tyr Gly Ser Ser Leu Glu Asp
        130                 135                 140

Asp Val Val Gly Asp Thr Ser Gly Tyr Tyr Gln Arg Met Leu Val Val
145                 150                 155                 160

Leu Leu Gln Ala Asn Arg Asp Pro Asp Ala Gly Ile Asp Glu Ala Gln
                165                 170                 175

Val Glu Gln Asp Ala Gln Ala Leu Phe Gln Ala Gly Glu Leu Lys Trp
                180                 185                 190

Gly Thr Asp Glu Glu Lys Phe Ile Thr Ile Phe Gly Thr Arg Ser Val
            195                 200                 205

Ser His Leu Arg Lys Val Phe Asp Lys Tyr Met Thr Ile Ser Gly Phe
        210                 215                 220

Gln Ile Glu Glu Thr Ile Asp Arg Glu Thr Ser Gly Asn Leu Glu Gln
225                 230                 235                 240

Leu Leu Leu Ala Val Val Lys Ser Ile Arg Ser Ile Pro Ala Tyr Leu
                245                 250                 255

Ala Glu Thr Leu Tyr Tyr Ala Met Lys Gly Ala Gly Thr Asp Asp His
                260                 265                 270

Thr Leu Ile Arg Val Met Val Ser Arg Ser Glu Ile Asp Leu Phe Asn
            275                 280                 285

Ile Arg Lys Glu Phe Arg Lys Asn Phe Ala Thr Ser Leu Tyr Ser Met
        290                 295                 300

Ile Lys Gly Asp Thr Ser Gly Asp Tyr Lys Lys Ala Leu Leu Leu Leu
305                 310                 315                 320

Cys Gly Glu Asp Asp
                325
```